US008613956B2

(12) United States Patent
Kleiman et al.

(10) Patent No.: US 8,613,956 B2
(45) Date of Patent: Dec. 24, 2013

(54) COSMETIC PARTICLES THAT TRANSFORM FROM HARD TO SOFT PARTICLES COMPRISING HYDROGENATED LONG-CHAIN TRIGLYCERIDE OILS

(75) Inventors: Robert Kleiman, Sun Lakes, AZ (US); James H. Brown, Scottsdale, AZ (US); Kelley Dwyer, Mesa, AZ (US); James S. Brown, Gilbert, AZ (US)

(73) Assignee: International Flora Technologies, Ltd., Chandler, AZ (US)

( * ) Notice: Subject to any disclaimer, the term of this patent is extended or adjusted under 35 U.S.C. 154(b) by 793 days.

(21) Appl. No.: 12/488,205

(22) Filed: Jun. 19, 2009

(65) Prior Publication Data

US 2009/0318554 A1 Dec. 24, 2009

Related U.S. Application Data

(60) Provisional application No. 61/074,872, filed on Jun. 23, 2008.

(51) Int. Cl.

| | |
|---|---|
| ***A61K 9/50*** | (2006.01) |
| ***A61K 9/14*** | (2006.01) |
| ***A61K 9/00*** | (2006.01) |
| ***A61K 8/02*** | (2006.01) |
| ***A61K 31/23*** | (2006.01) |
| ***C10M 159/06*** | (2006.01) |

(52) U.S. Cl.
USPC ........... 424/502; 424/400; 424/401; 424/489; 514/552; 508/451

(58) Field of Classification Search
None
See application file for complete search history.

(56) References Cited

U.S. PATENT DOCUMENTS

| | | | | |
|---|---|---|---|---|
| 5,011,680 | A * | 4/1991 | Suzuki et al. | 424/64 |
| 5,660,865 | A * | 8/1997 | Pedersen et al. | 426/99 |
| 6,197,286 | B1 * | 3/2001 | Scavone et al. | 424/65 |
| 2007/0116728 | A1 * | 5/2007 | Ioualalen et al. | 424/400 |
| 2011/0046034 | A1 * | 2/2011 | Stolz et al. | 510/130 |

FOREIGN PATENT DOCUMENTS

| | | | |
|---|---|---|---|
| DE | 4336407 | A1 | 4/1995 |
| EP | 1967173 | A1 | 9/2008 |
| FR | 2775441 | A1 | 9/1999 |
| WO | 9300065 | A1 | 1/1993 |
| WO | 0243671 | A2 | 6/2002 |

OTHER PUBLICATIONS

Orthobeads Product Specification; originally published Nov. 11, 2005.*
Orthobeads MSDS; originally published Feb. 1, 2001.*
Google search page showing publication dates for product spec. and MSDS; Sep. 26, 2011.*
http://www.desertwhale.com/fben_proddetail.cfm?prodid=23; Sep. 26, 2011.*
Abramovic et al. (Food Technol. Biotechnol.; pp. 63-70; 2005.*
US Patent Documents—none.*
Non-patent Documents—none.*

* cited by examiner

*Primary Examiner* — Robert A Wax
*Assistant Examiner* — Jeffrey T Palenik
(74) *Attorney, Agent, or Firm* — The Noblitt Group, PLLC

(57) ABSTRACT

Cosmetic particle compositions are provided which are adapted to form hard cosmetic particles that transform to soft cosmetic particles after their incorporation into topical formulations, particularly surfactant-based topical formulations. The composition includes one or more partially or fully hydrogenated triglyceride oils, at least 50% of which have at least 15% by weight fatty acid moieties with carbon chain lengths of $C_{18}$ or higher. Additives may be disposed in or on the hard cosmetic particles and delivered when the cosmetic particles are broken proximate a target such as the skin, hair or nails of a mammalian subject or another target. The transformable hard cosmetic particles permit the storage and shipment of intact cosmetic particles yet transform in situ to achieve the benefits of soft cosmetic particles.

17 Claims, No Drawings

COSMETIC PARTICLES THAT TRANSFORM FROM HARD TO SOFT PARTICLES COMPRISING HYDROGENATED LONG-CHAIN TRIGLYCERIDE OILS

CROSS-REFERENCES TO RELATED APPLICATIONS

This application claims the benefit of U.S. Provisional Application No. 61/074,872, filed Jun. 23, 2008.

FIELD OF THE INVENTION

The present invention generally relates to cosmetic particles, and more particularly relates to cosmetic particles adapted to form hard cosmetic particles of hydrogenated long-chain triglyceride oils that transform to soft cosmetic particles when formulated into topical formulations.

BACKGROUND OF THE INVENTION

Cosmetic particles are known in the art. Cosmetic particles can entrap a wide variety of additives including active agents for cosmetic and dermatological use to allow for better storage and/or controlled release of additives. Cosmetic particles can be formulated to be soft to add a visual and tactile appeal to the topical formulation in which they are incorporated, to deliver additives, and to deliver emolliency. Soft cosmetic particles may be rubbed into the skin leaving substantially no discernible debris and delivering additives to a user's skin, hair and/or nails. Cosmetic particles may also be formulated to be hard for visual appeal and to provide a mechanical exfoliating effect. Cosmetic particles typically maintain their structural integrity (i.e., generally do not substantially deform) when incorporated into a topical formulation.

The hardness of cosmetic particles is typically determined using a tactile scale that subjectively measures the amount of pressure applied between fingertips needed to deform the cosmetic particle. The hardness can range from very soft, where almost no pressure is needed to deform the cosmetic particle, to very hard where under normal pressure the beads will generally not deform but maintain their structural integrity and are rough on the skin, thus providing a mechanical exfoliating effect. Hard cosmetic particles typically deform only with considerable pressure.

Unfortunately, as almost no pressure is needed to deform soft cosmetic particles, cosmetic and dermatological agents may undesirably be released from soft cosmetic particles prior to their topical use. In addition, the storage and shipment of soft cosmetic particles may be problematic as they can lose their structural integrity and fuse into a single mass, because of, for example, the weight of overlying beads. However, while hard cosmetic particles generally maintain their structural integrity throughout storage and shipping and when incorporated into topical formulations, such hard cosmetic particle formulations typically do not deliver additives and provide the feel and emolliency features offered by soft cosmetic particles.

Accordingly, it is desirable to provide cosmetic particle compositions that advantageously permit hard cosmetic particles to transform to soft cosmetic particles after storage and shipment and after their incorporation into a topical formulation. It is also desirable that the transformed cosmetic particles can provide a tactile sensation and deliver emolliency to the skin, hair and nails of a mammalian subject or to another target. Furthermore, other desirable features and characteristics of the present invention will become apparent from the subsequent detailed description of the invention and the appended claims and this background of the invention.

BRIEF SUMMARY OF THE INVENTION

A cosmetic particle composition is provided that comprises one or more at least partially hydrogenated triglyceride oils, at least 50% of which have at least 15% by weight fatty acid moieties with carbon chain lengths greater than $C_{18}$, wherein said cosmetic particle composition may be adapted to form hard cosmetic particles that transform into soft cosmetic particles upon incorporation in a topical formulation. At least one additive may be entrapped, entrained, suspended or otherwise disposed within or on the hard cosmetic particle.

The cosmetic particle composition may comprise essentially 100% fully hydrogenated *Camelina sativa* seed oil that is formed into the hard cosmetic particles and transforms into soft cosmetic particles after introduction into a topical formulation. The transformed cosmetic particles may be adapted to deliver emolliency to the skin, hair, and/or nails of a mammalian subject or to another target.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of exemplary embodiments of the present invention.

Cosmetic particle compositions, in accordance with various exemplary embodiments, comprise one or more at least partially hydrogenated triglyceride oils, at least 50% of which have at least 15% by weight fatty acid moieties with carbon chain lengths greater than $C_{18}$. These cosmetic particle compositions may be adapted to form hard cosmetic particles that transform into soft cosmetic particles upon incorporation in a topical formulation. The cosmetic particle compositions may further comprise at least one additive entrapped, entrained, suspended or otherwise disposed within or on the hard cosmetic particles.

As used herein, "hard" cosmetic particles generally will not deform until more than normal pressure is applied and "soft" cosmetic particles will generally deform with less than normal pressure, as determined by a tactile scale that subjectively measures the amount of pressure applied between fingertips needed to deform the cosmetic particle. As used herein, "normal pressure" is that pressure typically applied without the exertion of considerable pressure and without the use of tools. The transformed cosmetic particles may be visibly intact but tactilely soft in the topical formulation.

The cosmetic particles may be substantially solid at room temperature, and may be provided in various shapes and sizes (but particularly in the form of spheres, microspheres or beads). As used herein, the term "particle" and "particles" refers to spheres, microspheres, beads, and/or the like, but also refers to any small-scale shape (e.g., a pellet, a toroid, an amorphous shape, etc.), even if not substantially spherical. In a representative exemplary embodiment, the cosmetic particles may comprise beads of a visible diameter on the order of about 50 microns to about 5,000 microns, and may be colored so as to be substantially visible in the topical formulation. These cosmetic particles, according to representative embodiments of the present invention, may be produced from partially hydrogenated and/or fully hydrogenated triglyceride oils derived from the seeds of various plant sources.

Non-limiting examples of suitable triglyceride oils that have at least 15% by weight fatty acid moieties with carbon chain lengths greater than $C_{18}$ include those derived from seeds of *Limnanthes alba* (meadowfoam), *Camelina sativa* (*camelina*), *Crambe abyssinica* (*crambe*), *Tropaeolum* species, High erucic acid rapeseed (HEAR), *eruca* species, *lunaria* species and most Cruciferae. If present, the other at least partially hydrogenated triglyceride oils in the cosmetic particle composition (i.e. those not having at least 15% by weight fatty acid moieties with carbon chain lengths greater than $C_{18}$) include canola oil, macadamia oil, olive oil, safflower oil, soybean oil, sunflower oil, and many others.

The triglyceride oils themselves are good emollients. Emollients are usually defined as any material that softens or smoothes the skin and which tends to reduce roughness, dryness, cracking, and irritation. In general, smoothing is believed to be effected by the penetration of the emollient into the surface layers of tissue (e.g., the stratum corneum and upper layers of the dermis, etc.), by rubbing and massaging action upon penetration.

The triglyceride oils may be partially hydrogenated to an iodine value of about ten or less or fully hydrogenated to an iodine value of less than one. Hydrogenation may be performed by any known methods. In a representative embodiment, all triglyceride oils that would be employed may be fully hydrogenated. The triglyceride oils form substantially hard cosmetic particles, with a substantially spherical shape. The cosmetic particles may be comprised of as much as 100% of the one or more at least partially hydrogenated triglyceride oils. The cosmetic particles produced may be hard, smooth, and generally not susceptible to deformation until more than normal pressure is applied.

In a representative embodiment, the triglyceride oil adapted to form the hard cosmetic particles in accordance with an embodiment of the invention comprises substantially fully hydrogenated *Camelina* seed oil. *Camelina* seed oil has at least 17% by weight of its fatty acid moities greater than 18 carbons in length. *Camelina* seed oil is generally derived from *Camelina sativa*. *Camelina* seed oil is relatively inexpensive as compared to many other seed oils and thus the cosmetic particles formed therewith are relatively inexpensive natural products.

In another representative and exemplary embodiment, the cosmetic particle composition further comprises at least one additive entrapped, entrained, suspended or otherwise disposed in or on the hard cosmetic particle. The at least one additive may be delivered via any cosmetic particle contemplated herein. Some additives may also be active agents. For example only, a 2% pigment (additive) may be a colorant for the cosmetic particles but 20% pigment may comprise an active agent because pigment may be left behind to change the appearance of the skin.

Non-limiting examples of additives include: alpha- and beta-hydroxy acids, amino acids, antibiotics, anti-fungals, antimicrobial agents, anti-perspirants, botanical extracts, colorants, cooling agents, cosmetically active ingredients, deodorants, depilatories, dermatologically active agents, detergents, dyes, emollients, essential oils, flavors, fragrance fixatives, fragrances, fruit and/or vegetable extracts and/or juices, glitters, hair relaxing agents, hair perming agents, humectants, hyaluronic acid, insect repellants, medicaments, natural emollients, nutritional supplements, peptide combinations, peptides, perfume, pharmaceutical preparations, pigments, polymerizing agents, polymers, preservatives, probiotics, provitamins, proteins, skin protectants, skin whiteners, slip agents (Teflon®, talc, etc.), soaps, styptics, sunless tanners, sunscreens, synthetic emollients, UV Blockers, vitamins, and warming agents.

The cosmetic particle composition may further comprise other additives including, but not limited to, tocopherols, colorants, and other oils from non-hydrogenated to fully hydrogenated oils, as well as preservatives and other cosmetic or dermatological ingredients. The non-hydrogenated oils may be added to control the starting and final texture of the cosmetic particle.

For example, in a representative and exemplary embodiment, the hydrogenated *Camelina* seed oil may be combined with *Copernicia cerifera* (carnauba) wax and *Simmondsia chinensis* seed oil (jojoba oil). Jojoba oil is composed almost exclusively of wax esters, with little or no triglycerides present. In a preferred embodiment, the cosmetic particle composition comprises about 98% by weight of substantially fully hydrogenated *Camelina* seed oil, about 1% by weight *Copernicia cerifera* (carnauba) wax and about 1% by weight *Simmondsia chinensis* seed oil.

In general, the at least one additive may be entrapped, entrained, suspended or otherwise disposed by known methods into or on the hard cosmetic particles comprising the one or more at least partially hydrogenated triglyceride oils at least 50% of which have at least 15% by weight fatty acid moieties with carbon chain lengths greater than $C_{18}$. The cosmetic particle composition generally comprises between about 50% to about 100% by weight at least partially hydrogenated triglyceride oil(s), representatively not less than about 70% by weight, at least 50% of which have at least 15% by weight fatty acid moities with carbon chain lengths greater than $C_{18}$ and about 0% to about 30% by weight additive(s). The preferred exemplary composition comprises about 80% by weight triglyceride oil(s) and about 20% by weight additive(s).

The cosmetic particle composition may generally be prepared as follows: Triglyceride oil(s) may be first hydrogenated by known methods to at most an iodine value of about 25% that of the original triglyceride oil or representatively to an iodine value of less than 1. The solid hydrogenated triglyceride oil may be mixed with the at least one additive. The triglyceride oil (and the at least one additive, if present) may be heated to its melting temperature (80 degrees Celsius is sufficient in most cases) to liquefy the oil. The liquefied oil (with the at least one additive, if present) may then be cooled and formed by known methods into hard cosmetic particles such as beads, spheres, microspheres or the like as described, for example, in U.S. Pat. No. 496,044, issued 25 Apr. 1893 (now expired) and U.S. Pat. No. 2,714,224, issued Aug. 2, 1955 (now expired).

In an exemplary embodiment, a cosmetic particle composition comprised of 100% *Camelina* seed oil may be prepared. In this case, the *Camelina* seed oil may be substantially fully hydrogenated and heated to its melting temperature of about 50 degrees Celsius to about 60 degrees Celsius to liquefy the oil. The liquefied material may then be cooled and formed by known methods into hard cosmetic particles comprised of 100% hydrogenated *Camelina* seed oil.

In yet another exemplary embodiment, a cosmetic particle composition comprised of about 80% by weight *Camelina* seed oil and 20% by weight additive may be prepared. The *Camelina* seed oil may be first hydrogenated and then melted with the additive. The liquefied mixture may then be cooled and formed by known methods into hard cosmetic particles of hydrogenated *Camelina* seed oil to additive in about an 80:20 ratio.

In yet another exemplary embodiment, a cosmetic particle composition comprised of about 75% by weight hydrogenated *Camelina* seed oil (a triglyceride oil having at least 15% by weight fatty acid moieties with carbon chain lengths of $C_{18}$ or higher), about 5% by weight hydrogenated *Moringa* oil, and about 20% by weight hydrogenated castor oil (both triglyceride oils but without the at least 15% by weight fatty acid moieties with carbon chain lengths of $C_{18}$ or higher) may be prepared. The triglyceride oils may be melted, then cooled and formed by known methods into hard cosmetic particles.

Hard cosmetic particles may be substantially suspended, for example, in the topical formulation, such as a gel, lotion, cream, emulsion, etc. to form a cosmetic composition adapted to deliver the cosmetic particles proximate to the surface of the skin, hair, and/or nails. Cosmetic particles in accordance with exemplary embodiments of the present invention may be incorporated into the topical formulation at a concentration of between about 0.01% to about 50%, representatively about 1% to about 5%, but these ranges may vary depending on the aesthetic and functional goals of the topical formulation. When incorporated into a topical formulation, hard cosmetic particles generally transform into soft cosmetic particles. The resulting soft cosmetic particles may be visibly intact but tactilely imperceptible in the topical formulation. The transformation may take a few days or a few weeks. In an exemplary embodiment, the temperature of the topical formulations may also be increased to between about 50 degrees Celsius to about 60 degrees Celsius to accelerate softening of the hard cosmetic particles.

In an exemplary embodiment, topical formulations generally include surfactant-based topical formulations. Non-limiting examples of surfactant-based topical formulations may include body washes, hand soaps, body polishers, facial scrubs, shampoos, or the like. The surfactant in surfactant-based formulations may include carboxylates, fatty alcohols, glucosides, poloxamers, polyethylene glycols, quaternary amines, sulfates, sulfonates, tweens, and betaines and other glycine derivatives.

The resultant soft cosmetic particles may be adapted to substantially disintegrate, rupture, burst or otherwise (collectively referred to herein as "break") upon mechanical shear forces applied by the user. In the case where there is no additive entrapped, entrained, suspended or otherwise disposed within or on the cosmetic particle, the broken soft cosmetic particles themselves deliver emolliency and may also provide tactile and visual appeal to the topical formulation. If the cosmetic particles include at least one additive, the broken soft cosmetic particles release at least one additive, thus liberating it to the surface of the skin, hair or nails. Upon liberation, at least one additive and one or more at least partially hydrogenated triglyceride oils may mix with the topical formulation to spread at least one additive substantially evenly over the surface of the skin, hair or nails of a mammalian subject.

The hard cosmetic particles formulated in accordance with exemplary embodiments as described herein may be delivered in a stable intact form to a topical formulation manufacturer, a cosmetic composition manufacturer, or the like that puts the hard cosmetic particles into a topical formulation. In one exemplary embodiment, the topical formulation may be warmed to accelerate the transformation to soft cosmetic particles for delivery of emolliency (from at least one or more triglyceride oils) and/or delivery of at least one additive.

Accordingly, cosmetic particle compositions adapted to form hard cosmetic particles that transform into soft cosmetic particles when added to a topical formulation are provided. The cosmetic particles remain hard during storage and shipping when their hardness is needed to protect the particles themselves and any additive entrapped, entrained, suspended or otherwise disposed within or thereon and transform to soft cosmetic particles only after their incorporation into a topical formulation. This ability to transform combines the desirable properties of a hard bead with the desirable properties of a soft bead.

While delivery of the cosmetic particles to the surface of the skin, hair and/or nails of a mammalian subject has been described, the invention is not so limited. The cosmetic particles may be used to deliver additives and emolliency to other targets for topical use such as to animals other than mammals, as well as to plants, furniture, or the like.

While at least one exemplary embodiment has been presented in the foregoing detailed description of the invention, it should be appreciated that a number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic particle composition comprising:

one or more at least partially hydrogenated triglyceride oils at least 50% of which have at least 15% by weight fatty acid moieties with carbon chain lengths greater than $C_{18}$, wherein:

said cosmetic particle composition is adapted to form hard cosmetic particles that transform into soft cosmetic particles upon incorporation in a topical formulation, and the one or more at least partially hydrogenated triglyceride oils comprises fully hydrogenated *Camelina saliva* triglyceride seed oil.

2. The cosmetic particle composition of claim 1, wherein the one or more at least partially hydrogenated triglyceride oils are present in an amount between about 70% to about 100% by weight of the cosmetic particle composition.

3. The cosmetic particle composition of claim 2, further comprising at least one additive in an amount no greater than about 30% by weight of the cosmetic particle composition.

4. The cosmetic particle composition of claim 3, wherein the one or more at least partially hydrogenated triglyceride oils are present in an amount of about 80% by weight and the at least one additive is present in an amount of about 20% by weight of the cosmetic particle composition.

5. The cosmetic particle composition of claim 1, wherein the one or more at least partially hydrogenated triglyceride oils further comprise at least partially hydrogenated triglyceride seed oils selected from the group consisting of *Limnanthes alba* (meadowfoani), *Crambe abyssinica* (crambe), *Trapaeolum* species, High erucic acid rapeseed (HEAR), *eruca* species, *lunaria* species and Cruciferae, and combinations thereof.

6. The cosmetic particle composition of claim 1, further comprising *Copernicia cerifera* (carnauba) wax and hydrogenated jojoba oil.

7. The cosmetic particle composition of claim 6, wherein the fully hydrogenated *Camelina sativa* triglyceride seed oil comprises about 98% by weight of the cosmetic particle composition, about 1% by weight of the *Copernicia cerifera* (carnauba) wax and about 1% by weight of the hydrogenated jojoba oil.

8. The cosmetic particle composition of claim 1, wherein the topical formulation further comprises a surfactant.

9. A cosmetic particle composition comprising:

a hard cosmetic particle comprised of one or more at least partially hydrogenated triglyceride oils at least 50% of which have at least 15% by weight fatty acid moieties with carbon chain lengths greater than $C_{18}$; and at least one additive disposed in or on the hard cosmetic particle, wherein:

the hard cosmetic particle transforms to a soft cosmetic particle upon incorporation into a topical formulation, and the one or more at least partially hydrogenated triglyceride oils comprise fully hydrogenated *Camelina sativa* triglyceride seed oil.

10. The cosmetic particle composition of claim 9, wherein the one or more at least partially hydrogenated triglyceride oils are present in an amount between about 70% to about 100% by weight of the cosmetic particle composition.

11. The cosmetic particle composition of claim 10, further comprising at least one additive in an amount no greater than about 30% by weight of the cosmetic particle composition.

12. The cosmetic particle composition of claim 11, wherein the one or more at least partially hydrogenated triglyceride oils are present in an amount of about 80% by weight and the at least one additive is present in an amount of about 20% by weight of the cosmetic particle composition.

13. The cosmetic particle composition of claim 9, wherein the one or more at least partially hydrogenated triglyceride oils further comprise at least partially hydrogenated triglyceride seed oils selected from the group consisting of *Limnanthes alba* (meadowfoam), *Crambe abyssinica* (crambe), *Tropaeolum* species, High erucic acid rapeseed (HEAR), *eruca* species, *lunaria* species and Crucifcrae, and combinations thereof.

14. The cosmetic particle composition of claim 9, further comprising *Copernicia cerifera* (carnauba) wax and jojoba esters.

15. The cosmetic particle composition of claim 14, wherein the fully hydrogenated *Camelina sativa* triglyceride seed oil comprises about 98% by weight of the cosmetic particle composition.

16. A cosmetic composition comprising:

a plurality of hard cosmetic particles comprised of one or more at least partially hydrogenated triglyceride oils at least 50% of which have at least 15% by weight fatty acid moieties with carbon chain lengths of greater than $C_{18}$; and a topical formulation, wherein:

said hard cosmetic particles are adapted to transform into soft cosmetic particles when introduced into the topical formulation to deliver emolliency to a target, and the one or more at least partially hydrogenated triglyceride oils comprise fully hydrogenated *Camelina sativa* triglyceride seed oil.

17. The cosmetic composition of claim 16, further comprising at least one additive disposed in or on at least one of the plurality of hard cosmetic particles.

* * * * *